United States Patent [19]
Cramer et al.

[11] Patent Number: 6,020,040
[45] Date of Patent: Feb. 1, 2000

[54] THERMAL PACK HAVING A PLURALITY OF INDIVIDUAL HEAT CELLS

[75] Inventors: Ronald Dean Cramer, Cincinnati; Leane Kristine Davis, Milford; William Robert Ouellette, Cincinnati, all of Ohio

[73] Assignee: The Procter & Gamble Company, Cincinnati, Ohio

[21] Appl. No.: 08/777,853

[22] Filed: Dec. 31, 1996

[51] Int. Cl.[7] .................................................... A61F 7/00
[52] U.S. Cl. ........................... 428/64.1; 252/67; 252/70; 428/66.4; 428/66.6; 428/68; 428/913; 607/114
[58] Field of Search ........................ 428/64.1, 68, 66.4, 428/66.6, 913; 126/263.02, 204; 62/530; 252/67, 70; 607/114

[56] References Cited

U.S. PATENT DOCUMENTS

| | | | |
|---|---|---|---|
| Re. 32,026 | 11/1985 | Yamashita et al. | 126/263 |
| 2,547,886 | 4/1951 | Poux | 62/1 |
| 2,562,121 | 7/1951 | Poux | 150/2.2 |
| 2,602,302 | 7/1952 | Poux | 62/1 |
| 3,463,161 | 8/1969 | Andrassy | 128/402 |
| 3,900,035 | 8/1975 | Welch et al. | 128/402 |
| 4,095,583 | 6/1978 | Peterson et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,516,564 | 5/1985 | Koiso et al. | 126/263 |
| 4,522,190 | 6/1985 | Kuhn et al. | 126/263 |
| 4,575,097 | 3/1986 | Brannigan et al. | 607/112 |
| 4,649,895 | 3/1987 | Yasuki et al. | 126/263 |
| 4,756,299 | 7/1988 | Podella | 126/263 |
| 4,860,748 | 8/1989 | Chiurco et al. | 128/399 |
| 4,886,063 | 12/1989 | Crews | 128/403 |
| 4,925,743 | 5/1990 | Ikeda et al. | 428/702 |
| 4,995,126 | 2/1991 | Matsuda | 5/421 |
| 5,025,777 | 6/1991 | Hardwick | 126/263 |
| 5,046,479 | 9/1991 | Usui | 126/204 |
| 5,062,269 | 11/1991 | Siegel et al. | 62/4 |
| 5,125,392 | 6/1992 | Hardwick | 126/263 |
| 5,179,944 | 1/1993 | McSymtz | 128/403 |
| 5,190,033 | 3/1993 | Johnson | 128/403 |
| 5,233,981 | 8/1993 | Miyashita | 607/114 |
| 5,342,412 | 8/1994 | Ueki | 607/114 |
| 5,366,491 | 11/1994 | Ingram et al. | 607/108 |
| 5,366,492 | 11/1994 | Ueki | 607/114 |
| 5,405,671 | 4/1995 | Kamin et al. | 428/69 |

FOREIGN PATENT DOCUMENTS

| | | |
|---|---|---|
| 0 370 600 A1 | 7/1989 | European Pat. Off. . |
| 160443 | 9/1983 | India . |
| 56-145846 | 11/1981 | Japan . |
| 57-170252 | 10/1982 | Japan . |
| 58-37075 | 3/1983 | Japan . |
| 3-100090 | 4/1991 | Japan . |
| 5-317188 | 12/1993 | Japan . |
| 6-1969 | 1/1994 | Japan . |
| 6-315498 | 11/1994 | Japan . |
| 6-343658 | 12/1994 | Japan . |
| 7-67907 | 3/1995 | Japan . |
| 7-124192 | 5/1995 | Japan . |
| 7-49042 | 5/1995 | Japan . |
| 7-194641 | 8/1995 | Japan . |
| 7-194642 | 8/1995 | Japan . |
| 8-98856 | 4/1996 | Japan . |
| 8-126656 | 5/1996 | Japan . |
| 2 205 496 | 12/1988 | United Kingdom . |
| 2 297 490 | 8/1996 | United Kingdom . |
| WO 94/00087 | 1/1994 | WIPO . |

OTHER PUBLICATIONS

U.S. application No. 08/777,830, Cramer et al., filed Dec. 31, 1996.
U.S. application No. 08/775,210, Cramer et al., filed Dec. 31, 1996.
U.S. application No. 08/777,642, Cramer et al., filed Dec. 31, 1996.
U.S. application No. 08/777,856, Cramer et al., filed Dec. 31, 1996.
U.S. application No. 08/496,565, Ouellette et al., filed Jun. 29, 1995.
U.S. application No. 08/748,203, Ouellette et al., filed Nov. 11, 1996.
U.S. application No. 08/496,716, Burkett et al., filed Jun. 29, 1995.
U.S. application No. 08/746,359, Burkett et al., filed Nov. 11, 1996.
U.S. application No. 08/496,373, Ouellette et al., filed Jun. 29, 1995.
U.S. application No. 08/686,800, Ouellette et al., filed Jul. 26, 1996.
U.S. application No. 08/672,166, Viltro et al., filed Jun. 27,1996.
U.S. application No. 08/754,947, Burkett et al., filed Nov. 21, 1996.
U.S. application 08/623,752, White, filed Mar. 29, 1996.

*Primary Examiner*—Nasser Ahmad
*Attorney, Agent, or Firm*—Loy M. White; Douglas C. Mohl; T. David Reed

[57] ABSTRACT

The present invention relates to disposable thermal packs comprising a unified structure having at least one continuous layer of a semirigid material which softens when heated. The thermal packs also comprise a plurality of individual heat cells, which typically comprise an exothermic composition, spaced apart and fixedly attached across the unified structure. The material of the continuous layer or layers provide sufficient rigidity to maintain structural support of the heat cells, to prevent unacceptable stretching of structures of the continuous layer or layers during processing or use of the thermal packs, and to ensure child resistance, while also providing good overall drape characteristics when heated. The thermal packs, when incorporated into body wraps, pads, and the like, provide uniform heat coverage by having excellent conformity with various body forms.

23 Claims, No Drawings

THERMAL PACK HAVING A PLURALITY OF INDIVIDUAL HEAT CELLS

TECHNICAL FIELD

The present invention relates to a disposable thermal pack comprising a unified structure having at least one continuous layer of a semirigid material which softens when heated. The thermal pack also comprises a plurality of individual heat cells, which typically comprise an exothermic composition, spaced apart and fixedly attached across the unified structure. The material of the continuous layer or layers provide sufficient rigidity to maintain structural support of the heat cells, to prevent unacceptable stretching of structures of the continuous layer or layers during processing or use of the thermal pack, and to ensure child resistance, while also providing good overall drape characteristics when heated. The thermal pack, when incorporated into body wraps, pads, and the like, provides uniform heat coverage by having excellent conformity with various body forms.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like. These treatments include the use of whirlpools, hot towels, hydrocollators, heating pads and elastic compression bands. Many of these devices employ reusable thermal packs containing, e.g., water and microwaveable gels. In general, such devices which require the thermal source to be replenished are inconvenient to use. Further, many of these thermal units or devices do not provide long lasting heat and also do not maintain a consistent temperature over long periods of time. Depending on the length of exposure, the skin temperature needs to be maintained from about 35° C. to about 55° C., preferably from about 36° C. to about 45° C., more preferably from about 37° C. to about 43° C., and most preferably from about 38° C. to about 42° C., to achieve the desired therapeutic benefits.

The beneficial therapeutic effects from this administration of heat diminish after the heat source is removed. Therefore, depending on the temperature, it is desirable to provide a sustained heat source to the afflicted area for as long as possible, i.e., from about twenty minutes to about twelve hours, preferably from about four hours to about twelve hours, most preferably from about eight hours to about twelve hours. Disposable heat packs based on iron oxidation, such as those described in U.S. Pat. Nos. 4,366,804, 4,649,895, 5,046,479 and Re. 32,026, are known and can provide long-lasting heat. However, such devices have proven not totally satisfactory because many of these devices cannot maintain a consistent and controlled temperature and/or such thermal devices are bulky and have unsatisfactory physical dimensions which hinder their effectiveness. Specifically, such devices cannot be easily incorporated into wraps which can comfortably conform to various body contours, and hence, they deliver short duration, inconsistent, inconvenient and/or uncomfortable heat application to the body.

The present inventors have discovered that the use of thin, flexible materials and a plurality of individual heat cells spaced apart for their thermal pack improves temperature control and overcomes many of the past difficulties, but have introduced some new difficulties. Though inherently more flexible, thinner materials, when combined with a plurality of individual heat cells, can lead to difficulty retaining sufficient rigidity to maintain structural support of the heat cells in an unsupported format, prevent unacceptable stretching of structures of the thin, flexible material during processing or use, and/or ensure child resistance.

For example, thermal packs made of a 25 $\mu$m thick low density polyethylene (LDPE) film, which has low rigidity, and a plurality of heat cells spaced apart, drape well around various body parts and provide comfortable heat application to the body. However, thermal packs comprising a 25 $\mu$m thick LDPE film can be opened relatively easily by children, the polyethylene can stretch during processing tending to decrease process reliability, the polyethylene can stretch in use leading to deleterious product performance, and the polyethylene can cause the heat cell structure to collapse upon itself due to inadequate upward support between the heat cells when used on an incline or vertically in an unsupported format.

The present inventors have similarly discovered that the use of thin but overly rigid materials, and a plurality of individual heat cells spaced apart for their thermal pack, improves temperature control, alleviates unacceptable stretching of the material during processing or use, restores structural support of the heat cells, and restores sufficient child resistance. However, thermal packs made of the thin but overly rigid material do not drape well around various body parts, even when heated, leading to a less than optimal comfortable application of heat to the body. That is, thermal packs made of overly rigid materials conform poorly to body locations, particularly body locations which require the material to bend in three dimensions during use.

For example, thermal packs made of a 40 gram/m² polypropylene spunbond nonwoven, which is extrusion coated with low density polyethylene or ethylene vinyl acetate copolymer (EVA) at a basis weight thickness of 50 to 75 $\mu$m, is thin enough to be flexible and yet sufficiently rigid so that vertical structural support, stretching, and child resistance are not concerns, are overly rigid and conform poorly to specific body locations, even when heated; particularly those body locations which require the material to bend in three dimensions.

The present inventors have discovered that a disposable thermal pack comprising at least one continuous layer of a material which is sufficiently rigid in specific areas of the thermal packs, yet which softens in between such areas during use, preferably comprising a semirigid coextruded film of polypropylene and EVA, together with a plurality of individual heat cells, having an exothermic composition, preferably comprising a specific iron oxidation chemistry and having specific physical dimensions and fill characteristics, spaced apart and fixedly attached across the thermal pack, possess some or all of the desired properties of both the thin, overly rigid materials and the thin, flexible materials mentioned above. Active heat cells, that is, heat cells having a temperature of from about 39° C. to about 60° C., preferably from about 40° C. to about 48° C., more preferably from about 41° C. to about 47° C., most preferably from about 42° C. to about 45° C., preferably soften narrow portions of the continuous layer or layers of semirigid material which immediately surround the heat cells. All remaining portions of the continuous layer or layers which surround the softened portions remain more rigid. The narrow, softened portions act as hinges between each heat cell and the remaining, cooler, more rigid portions, bending preferentially more than either the heat cell or the more rigid portions. This results in thermal packs which possess sufficient rigidity to maintain structural support of the heat cells, to prevent unacceptable stretching of structures of the continuous layer or layers during processing or use, and to ensure child resistance, while still maintaining good overall drape characteristics when heated. The thermal packs, when incorporated into body wraps, pads, and the like, provide uniform heat coverage by having excellent conformity with various body forms.

The present inventors have also discovered that undesirable, uninterrupted fold lines across the disposable thermal pack, or select regions thereof, which comprise a semirigid coextruded film of polypropylene and EVA that does not drape well and which may only drape two dimensionally, can be minimized or eliminated altogether by selectively placing the heat cells into positions relative to each other which are sufficiently close so as to block some or all possible axes which otherwise would have passed uninterrupted between the heat cells, through the thermal pack, or select regions thereof. In addition to the placement of heat cells to minimize or eliminate undesirable, uninterrupted fold lines, active heat cells soften narrow portions of the continuous layer or layers of material which immediately surround the heat sources, while all remaining portions of the continuous layer or layers of material which immediately surround the softened portions remain more rigid. The narrow, softened portions act as hinges, between each heat cell and the remaining more rigid portions, bending preferentially more than either the heat cell or the more rigid portions. Placement of the heat cells into positions relative to each other which are sufficiently close so that the number of axes which pass uninterrupted, between the heat cells coupled with the narrow softened portions, immediately surrounding the heat cells, acting as hinges, causes the disposable thermal pack to fold along a multiplicity of short interconnected fold lines oriented in a number of different directions relative to each other. Folding along a multiplicity of interconnected fold lines results in good overall drape characteristics. When heated, as described above, the semirigid material minimizes or effectively eliminates an undesirable, two dimensional drape characteristic across the thermal pack, or select regions thereof, thereby converting the thermal pack, or select regions thereof, to possess an apparent three dimensional drape characteristic.

It is therefore an object of the present invention to provide a disposable thermal pack which comprise a unified, structure having at least one continuous layer of semirigid material which has different stiffness characteristics over a range of temperatures and a plurality of individual heat cells, which provide a controlled and sustained temperature and which reach their operating temperature range relatively quickly. The heat cells are spaced apart and fixedly attached across the unified structure of the disposable thermal pack.

It is a further object of the present invention to provide a thermal pack which can be easily incorporated into disposable body wraps, having good overall drapability while maintaining sufficient rigidity to maintain structural support of the heat cells, to prevent unacceptable stretching of the continuous layer or layers during processing or use, and/or ensure child resistance.

It is a still further object on the present invention to provide a thermal pack which adapt to a wide variety of body contours by minimizing or eliminating undesirable, two dimensional drape characteristics across the thermal pack to provide consistent, convenient and comfortable heat application.

These objectives and additional objectives will become readily apparent from the detailed description which follows.

SUMMARY OF THE INVENTION

The disposable thermal pack of the present invention comprise a unified structure containing at least one continuous layer of a material which is semirigid at a temperature of about 25° C., and substantially less rigid at a temperature of about 45° C.

The disposable thermal pack of the present invention also comprise a plurality of individual heat cells, which preferably comprise an exothermic composition, preferably comprising an iron oxidation chemistry, spaced apart and fixedly attached to the structure of the disposable thermal pack.

The continuous layer or layers of material of the present invention preferably comprise a coextruded film, wherein one side comprises polypropylene, preferably from about 10% to about 90%, more preferably from about 40% to about 60%, of the total thickness of the film, and the other side comprises a tie-layer of a low melt temperature polymer, such as EVA, having a combined basis weight thickness of from about 20 $\mu$m to about 30 $\mu$m, preferably about 25 $\mu$m.

The heat cells may be placed into positions along the continuous layer or layers, relative to each other, sufficiently close so that the number of axes which pass uninterrupted between the heat cells causes the thermal pack to fold along a multiplicity of short interconnected fold lines oriented in a number of different directions relative to each other minimizing or eliminating undesirable, two dimensional drape characteristics across the thermal pack and converting the thermal pack to possess apparent three dimensional drape characteristics.

All percentages and ratios used herein are by weight of the total composition, and all measurements made at 25° C., unless otherwise specified.

DETAILED DESCRIPTION OF THE INVENTION

The thermal pack of the present invention comprise at least one continuous layer of a material, which exhibits specific thermophysical properties. The material is semirigid when at room temperature, i.e., about 25° C., or below, but softens and becomes substantially less rigid when heated to about 45° C. Therefore, when heat cells, which are fixedly attached to the structure of the thermal pack, are active, that is at a heat cell temperature of from about 39° C. to about 60° C., preferably from about 40° C. to about 48° C., more preferably from about 41° C. to about 47° C., and most preferably from about 42° C. to about 45° C., the narrow portion of the continuous layer or layers of material immediately surrounding each heat cell softens and acts as a hinge between the heat cell and the remaining more rigid portion of the continuous layer or layers, bending preferentially more than either the heat cell or the cooler, more rigid portion. This results in a thermal pack which possesses sufficient rigidity to maintain structural support of the heat cells and prevent unacceptable stretching of structures of the continuous layer or layers during processing or use, while still maintaining good overall drape characteristics when heated. The thermal pack of the present invention, which when incorporated into body wraps, pads, and the like, which easily adapt to a wide variety of body contours, provides consistent, convenient, and comfortable heat application, and an excellent conformity with body forms, while retaining sufficient rigidity to ensure child resistance.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Agglomerated pre-compaction composition", as used herein, means the mixture of dry powdered ingredients, comprising iron powder, carbonaceous powder, metal salt (s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Semirigid material", as used herein, means a material which is rigid to some degree or in some parts and exhibits a toughness to maintain structural support of the heat cells in an unsupported format, and/or to prevent unacceptable stretching of structures of the material during processing or use and/or to ensure child resistance while still maintaining good overall drape characteristics when heated.

"Two dimensional drape", as used herein, means drape which occurs across a continuous layer or layers, across a thermal pack, or across a select region of a layer or layers, or thermal pack, exclusively along one axis, i.e., one fold line forms, at the expense of other fold lines in response to gravitational pull or other modest forces.

"Three dimensional drape", as used herein, means drape which simultaneously occurs across a continuous layer or layers, across a thermal pack, or across a select region of a layer or layers, or thermal pack, among two or more axes in response to gravitational pull or other modest forces.

Continuous Layer(s)

The continuous layer or layers of the present invention is a thermoplastic material which is semirigid at a temperature of about 25° C. and which softens, i.e., becomes substantially less rigid, at a temperature of about 45° C. Different materials may be capable of satisfying the specified requirement provided that the thickness is adjusted accordingly. Such materials may include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone or coextruded with a low melt temperature polymer including, but not limited to, ethylene vinyl acetate copolymer, low density polyethylene, and mixtures thereof. A particularly suitable and preferred material for the continuous layer or layers is a coextruded film of polypropylene and EVA having a total film thickness of about 25 $\mu$m wherein the polypropylene comprises from about 10% to about 90% and the EVA tie-layer comprises from about 90% to about 10% of the total film thickness. Preferably, the polypropylene comprises from about 40% to about 60% of the total film thickness. This material is available from Clopay Plastic Products, Cincinnati, Ohio, as P18-3161. When the polypropylene/EVA coextruded film is used to make the thermal packs and/or heat cells of the present invention, the polypropylene side is oriented to the outside (i.e., away from the exothemric composition).

Heat Cells

The thermal pack of the present invention comprises a plurality of individual heat cells fixedly attached to the unified structure of the thermal pack. These heat cells are spaced apart from each other and each heat cell functions independently of the rest of the heat cells. While the heat cells may comprise any suitable composition providing heat, such as exothermric compositions, microwaveable compositions, heat of crystallization compositions, and the like, the preferred heat cell contains a densely packed, particulate exothermic composition which substantially fills the available cell volume within the cell reducing any excess void volume thereby minimizing the ability of the particulate matter to shift within the cell. Alternatively, the exothermic composition may be compressed into a hard tablet before being placed in each cell. Because the heat generating material is densely packed or compressed into a tablet, the heat cells are not readily flexible. Selective placement of the heat cells into positions relative to each other and sufficiently close may block some or all possible axes which otherwise would have passed uninterrupted between the heat cells, through the thermal packs, or select regions thereof. In addition to the placement of heat cells to minimize or eliminate undesirable, uninterrupted fold lines, active heat cells soften narrow portions of the continuous layer or layers of material which immediately surround the heat sources, while all remaining portions of the continuous layer or layers of material which immediately surround the softened portions remain more rigid. The narrow, softened portions act as hinges, between each heat cell and the remaining cooler, more rigid portions, bending preferentially more than either the heat cell or the cooler, more rigid portions. Placement of the heat cells into positions relative to each other which are sufficiently close so that the number of axes which pass uninterrupted, between the heat cells coupled with the narrow softened portions, immediately surrounding the heat cells, acting as hinges, causes the disposable thermal pack to fold along a multiplicity of short interconnected fold lines oriented in a number of different directions relative to each other. Folding along a multiplicity of interconnected fold lines results in good overall drape characteristics. When heated, as described above, the semirigid material minimizes or effectively eliminates an undesirable, two dimensional drape characteristic across the thermal pack, or select regions thereof, thereby converting the thermal packs, or select regions thereof, to possess an apparent three dimensional drape characteristic. Therefore, the spacing apart of the cells and the material, as described above, between the heat cells allows the thermal pack of the present invention to conform with various body forms.

The exothermic composition preferably comprises a mix of chemical compounds that undergo an oxidation reaction during use. The mix of compounds typically comprises iron powder, carbon, a metal salt(s), and water. Mixtures of this type react when exposed to oxygen, providing heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are usefull in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

Preferably at least 50%, more preferably 70%, even more preferably 80% and most preferably 90% of all of the particles by weight of the particulate exothermic composition of the present invention have a mean particle size of less than 200 µm, preferably less than 150 µm.

The above-mentioned components of the composition are blended using conventional blending techniques. Suitable methods of blending these components are described in detail in U.S. Pat. No. 4,649,895 to Yasuki et al., issued Mar. 17, 1987 which is incorporated by reference herein. For example, carbon is added to a blender or mixer, followed by a small amount of the total water and this combination is mixed. Usually enough water is added to assist in blending while avoiding escalated corrosion. Mixing is stopped and vermiculite is added to the carbon. Mixing is resumed until all the components are mixed thoroughly and iron powder is added and mixed. The composition is then blended until thoroughly mixed. Sodium chloride and the remaining water are mixed to form a brine solution which is then added to the particulate composition during construction of the heat cell.

In the alternative, the above-mentioned components of the composition can be blended using conventional blending techniques. For example, carbon is added to a blender or mixer, followed by a small amount of the total water and this combination is mixed. Usually enough water is added to assist in blending while avoiding escalated corrosion. Mixing is stopped and vermiculite and sodium chloride are added to together. Mixing is resumed until all the components are mixed thoroughly and iron powder is added and mixed. The composition is then blended until thoroughly mixed. Additional water is added to the particulate composition during construction of the heat cell.

Alternatively to the above described particulate exothermic composition, the exothermic composition may be formed into agglomerated granules, direct compacted into compaction articles such as granules, pellets, tablets, and/or slugs, and mixtures thereof.

The exothermic composition of these agglomerated granules and/or compaction articles comprises iron powder, dry powdered carbonaceous material, an agglomeration aid, and a dry binder. Additionally, a metal salt, is added to the dry mix or subsequently as an aqueous/brine solution.

As described above for the particulate exothermic composition, there is no particular limitation to the purity, kind, etc. of the iron powder used in the agglomerated granules and/or compaction articles, so long as it can be used to produce heat-generation with electrically conducting water and air. Suitable sources for iron powder include cast iron powder, reduced iron powder, electrolytic iron powder, scrap iron powder, pig iron, wrought iron, various steels, iron alloys, and the like and treated varieties of these iron powders. Typically, the iron powder comprises from about 30% to about 80%, preferably from about 40% to about 70%, most preferably from about 50% to about 65% by weight, of the agglomerated pre-compaction compositions.

Likewise, there is no limitation to the kinds of active carbon used, however, the preferred active carbon has superior water holding capabilities and the different carbons may be blended to reduce cost. Active carbon prepared from coconut shell, wood, charcoal, coal, bone coal, etc. are useful, but those prepared from other raw materials such as animal products, natural gas, fats, oils and resins are also useful in the agglomerated granules and/or compaction articles. Typically, activated carbon, non-activated carbon, and mixtures thereof, comprises from about 3% to about 20%, preferably from about 5% to about 15%, most preferably from about 6% to about 12% by weight, of the agglomerated pre-compaction compositions.

The metal salt is typically added as a dry powder to the exothermic composition before agglomeration, but may also be added to the exothermic compositions in the water as a salt (brine) solution. Metal salts which are useful are the alkali, alkaline earth, and transitional metal salts which includes sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Other suitable alkali, alkaline earth, and transition metal salts also exist which can be used, alone or in combination. Also, carbonate salts, acetate salts, nitrates, nitrites and other salts can be used. Typically, the metal salt(s) comprises from about 0.5% to about 10%, preferably from about 1% to about 8%, most preferably from about 2% to about 6% by weight, of the agglomerated pre-compaction compositions.

Maintaining the content uniformity of powders after mixing and prior to compaction is a primary concern. Therefore, the essential reaction chemistry is agglomerated using low levels of agglomeration aids prior to the addition of dry binders necessary for a hard compaction. Examples of agglomeration aids which are useful, but not limited to, include gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup. The preferred agglomerating aids are crystallizing sorbitol, amorphous sorbitol, corn syrup, maltitol syrup, and mixtures thereof. Typically, agglomeration aids comprise from about 0% to about 9%, preferably from about 0.5% to about 8%, more preferably from about 0.6% to about 6%, most preferably from about 0.7% to about 3% by weight, of the agglomerated pre-compaction compositions.

Since iron and carbon do not compact easily, binders which are capable of binding fine powder under dry conditions and at low concentration while producing a non-friable granulation, must be added to the exothermic compositions. Dry binders which are useful, but not limited to, include maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate. The preferred dry binding agent is microcrystalline cellulose. The amount of dry binder added depends on the degree of hardness desired, however, dry binders typically comprise from about 0% to about 35%, preferably from about 4% to about 30%, more preferably from about 7% to about 20%, most preferably from about 9% to about 15% by weight, of the agglomerated pre-compaction compositions.

The aqueous solution typically used in the compositions comprising agglomerated granules and/or direct compacted articles is water. Water may also serve as a solvent for dissolving and carrier for delivering the metal salt and added in the form of a brine solution. The water used herein may be from any appropriate source. There is no particular limitation to its purity, kind, etc. The amount of aqueous solution added to the exothermic compositions depends on the type and amount of iron to be added, however, the aqueous solution typically, comprises from about 10% to about 50%, preferably from about 15% to about 40%, most preferably from about 15% to about 30%, by weight of the compaction articles.

In addition to the above described components of the agglomerated granules and/or compaction articles, other components may also be added as appropriate. These include additional water-holding materials, disintegrants, lubricants, oxidation reaction enhancers, compounds to prevent the generation of gases, fillers, anti-caking agents, thickeners, surfactants, and extending agents. Such additional components are previously described herein.

Heat cells comprising agglomerated granules are typically made using conventional blending techniques and agglomerated into granules. For example, powdered carbon and a metal salt are added to a blender or mixer, and blended into a uniform dry mixture. An additional water-holding material is added and the composition is mixed until uniform. For this particular method of making heat cells, dry binders may be optionally added to the composition along with the additional water-holding material. powdered iron is added and the mixture is again blended until uniform. An agglomeration aid is then added to the blended powders. The composition is mixed until a light agglomeration is formed and no dust appears. The granules may be placed directly into a heat cell pocket or direct compacted into compaction articles. These agglomerated granules are soft, porous, easily wetted, and less dense particles, which may be sufficient in some applications.

Heat cells comprising compaction articles are preferably made by direct compaction of the dry ingredients into articles such as hard granules, pellets, tablets, and/or slugs. For example, powdered carbon and a metal salt are added to a blender or mixer, and blended into a uniform dry mixture. Powdered iron and a disintegrant are added to the carbon/salt mixture and blended until the new mixture is uniform. An agglomeration aid is added to the blended powders. The composition is mixed until a light agglomeration is formed and no dust appears. An additional water-holding material is then added to the agglomeration. Gentle mixing continues until the additional water-holding material is evenly dispersed in the agglomeration. A dry binder is added to the agglomeration and the composition is mixed until uniform. The mixture is then transferred to a rotary tablet press and compressed into disk shaped tablets having a hole passing perpendicular through the middle of the top and bottom surfaces, having concaved top and bottom surfaces, i.e., double whisper design, or other shapes forming a reservoir conducive to holding water.

In a variation of the method described above, the precompaction composition may be compressed into a slug, having no particular shape, or a tablet which lacks the hole or reservoir, rather, the tablet comprises any standard tablet configuration including spherical, convexed shallow face, convexed standard face, convexed deep face, flat face, and capsule, flat edge, beveled edge, oval, and modified ball.

Suitable methods of making tablets and/or slugs are described in detail in Chapter 89, "Oral Solid Dosage Forms", *Remington's Pharmaceutical Sciences*, 18th Edition, (1990), pp. 1634–1656, Alfonso R. Gennaro, ed., incorporated herein by reference in its entirety. Any conventional tableting machine and compression pressures, up to the maximum provided by the machine can be used.

Activation of each cell is accomplished by injecting water or salt solution, i.e., by needle, through the oxygen permeable layer into the hole or reservoir in the middle of the tablet, or into the granular composition. Since the heat cell will begin to generate heat shortly after activation if exposed to air, the thermal pack is placed immediately into an oxygen impermeable secondary package, which may be optionally evacuated of oxygen, and then sealed. This secondary packaging is described below. Alternatively, water or salt solution can be added to exothermic composition prior to the application of the second continuous layer which forms the heat cell.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. The preferred shape of the tablet/slug comprises a disk shaped geometry, having a concaved (whisper) configuration to the top and/or bottom of the tablet. The more preferred shape of the tablet/slug, however, comprises a disk shaped geometry, having a hole perpendicular to, and through the middle of the top and bottom of the tablet A water-carrying material having hydrous property and flexibility such as superabsorbents, a spongy body, paper, synthetic resin-foam, rubber, cellulose, and the like may be placed in the hole or reservoir to gradually supply the water to the compressed particulate composition to prolong the exothermic reaction.

The size of the disk is limited only by the size of the punches and die available and/or used in the tableting machine, as well as the size of the heat cell pocket. However, the disk typically has a diameter of from about 0.2 cm to about 10 cm, preferably from about 0.5 cm to about 8 cm, more preferably from about 1 cm to about 5 cm, and most preferably from about 1.5 cm to about 3 cm and a height of from about 0.08 cm to about 0.7 cm, preferably from about 0.15 cm to about 0.6 cm, more preferably from about 0.2 cm to about 0.55 cm, and most preferably from about 0.2 cm to about 0.5 cm. The hole or reservoir should be large enough to substantially hold the prescribed amount of water and/or the water-carrying material. Typically, the hole has a diameter of from about 0.1 cm to about 1 cm, preferably from about 0.2 cm to about 0.8 cm, and more preferably from about 0.2 cm to about 0.5 cm.

The compaction articles of the present invention are compressed to the hardest possible mechanical strength to withstand the shocks of handling in their manufacture, packing, shipping, and dispensing. The compaction articles are typically compressed to a density of greater than about 1 $g/cm^3$, preferably from about 1 $g/cm^3$ to about 3 $g/cm^3$, more preferably from about 1.5 $g/cm^3$ to about 3 $g/cm^3$, and most preferably from about 2 $g/cm^3$ to about 3 $g/cm^3$.

Heat cells comprising the above described components are typically formed by adding a fixed amount of a particulate exothermic composition or compaction article(s) to a pocket or pockets made in a first continuous layer. A second continuous layer is placed over the first continuous layer, sandwiching the particulate exothermic composition or compaction article(s) between the two continuous layers which are then bonded together, preferably using a low heat, forming a unified, laminate structure. Preferably, each heat cell has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

Pockets are typically made in the first continuous layer by thermoforming, mechanical embossing, vacuum embossing, or other acceptable means. A preferred method for use herein is thermoforming which is described in "Thermoforming", *The Wiley Encyclopedia of Packaging Technology*, pp. 668–675 (1986), Marilyn Bakker, ed., incorporated herein by reference in its entirety. Typically, the first continuous layer is placed on a mold having a plurality of appropriately-shaped indentations spaced apart. The first continuous layer is then heated and a vacuum is applied such that the first continuous layer is drawn into and conforms to the mold. The particulate composition or compaction article(s) is placed on top of the first continuous layer directly into the heat/vacuum-formed pocket(s). As the particulate composition or compaction article(s) is dropped into the pocket(s), it may be held in place by gravity, vacuum, and/or a magnetic force in the bottom of the mold indentation. The second continuous layer is then placed over the first continuous layer, such that the particulate composition or compaction article(s) is between the two continuous layers. The particulate composition or compaction article(s) is sealed between the first and second continuous layers, preferably using a low heat, and the vacuum is removed.

A more preferred method of preparing individual heat cells uses vacuum only to form the pockets. That is, vacuum is used to draw the first continuous layer to a mold having a plurality of appropriately-shaped indentations spaced apart. The particulate composition or compaction article(s) is placed on top of the first continuous layer directly into the vacuum-molded pocket(s). As the particulate composition or compaction article(s) is dropped into the vacuum formed pocket(s), it is held in place by gravity, vacuum, and/or a magnetic force in the bottom of the mold indentation. The second continuous layer is then placed over the first continuous layer, such that the particulate composition or compaction article(s) is between the two continuous layers. The particulate composition or compaction article(s) is sealed between the first and second continuous layers, preferably using low heat. The vacuum is then removed, allowing the first continuous layer to form a tightly packed heat cell(s).

The heat cells may also be prepared by using magnetic transfer of a fixed amount of the particulate exothermic composition to the pockets as described in Japanese Kokoku Patent No. HEI 05/081261 to Watabe, et al., issued Jan. 7, 1992, which is incorporated herein by reference in its entirety.

The finished heat cell can have any geometric shape, e.g., disk, triangle, pyramid, cone, sphere, square, cube, rectangle, rectangular parallelepiped, cylinder, ellipsoid and the like. The preferred shape of the heat cells manufactured according to the present invention, comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells manufactured according to the present invention have a height of from about 0.15 cm to about 1 cm, preferably from about 0.3 cm to about 0.9 cm, more preferably from about 0.4 cm to about 0.8 cm, and most preferably from about 0.4 cm to about 0.7 cm resulting in a cell volume of from about 0.0047 cm$^3$ to about 79 cm$^3$, preferably from about 0.05 cm$^3$ to about 46 cm$^3$, more preferably from about 0.3 cm$^3$ to about 16 cm$^3$, and most preferably from about 0.7 cm$^3$ to about 5 cm$^3$. Alternatively, the heat cells having geometric shapes other than a disk shape may have a width at its widest point of from about 0.15 cm to about 20 cm, preferably from about 0.3 cm to about 10 cm, a height at its highest point of from about 0.15 cm to about 5 cm, preferably from about 0.3 cm to about 1 cm, and a length of from about 1 cm to about 20 cm, preferably from about 5 cm to about 10 cm.

The ratio of fill volume to cell volume is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability can be provided by selecting materials for the first and second continuous layers forming the pockets, and/or covering layer, that have the specifically desired permeability properties. The desired permeability properties may be provided by microporous films or by films which have pores or holes formed therein. The formation of holes/pores may be via extrusion cast/vacuum formation or by hot or cold needle aperturing. For example, at least one of the continuous layers described above may be apertured prior to heat cell construction. This aperturing is preferably achieved via the use of an array of hot needles having tapered points and base diameters of from about 0.2 mm to about 2 mm, preferably from about 0.4 mm to about 1.5 mm, more preferably from about 0.8 mm to about 1.0 mm, and a length of about 6 mm. These needles are heated to a temperature of from about 90° C. to about 400° C. and pierce the material to a depth of from about 200 $\mu$m to about 500 $\mu$m. A needle density of from about 2 to about 30 pins per square centimeter, preferably from about 4 to about 10 needles per square centimeter provides the desired permeability properties which control the rate of the chemical oxidation and hence the thermal output of the heat cells.

Oxygen permeability can also be provided in the present invention after the continuous layers have been bonded together enclosing the exothermic composition in the pocket between them, by perforating one side of the heat cells with aeration holes using, for example, at least one pin, preferably an array of from about 20 to about 60 pins having tapered points and diameters of from about 0.2 mm to about 2 mm, preferably from about 0.4 mm to about 0.9 mm. The pins are pressed through one side of the continuous layer material to a depth of from about 2% to about 100%, preferably from about 20% to about 100%, and more preferably from about 50% to about 100% into the particulate exothermic composition.

These hole configurations typically provide an oxygen diffusion into the heat cell during oxidation of the exothermic composition of from about 0.01 cc O$_2$/min./5 cm$^2$ to about 15.0 cc O$_2$/min./5 cm$^2$ (at 21° C., 1 ATM), preferably from about 0.9 cc O$_2$/min./5 cm$^2$ to about 3 cc O$_2$/min./5 cm$^2$ (at 21° C., 1 ATM). Although there is preferably provided aeration holes in the upper covering continuous layer, it is also possible to provide aeration holes in the lower continuous layer, and/or both.

The velocity, duration, and temperature of the thermogenic oxidation reaction of the particulate exothermic composition can be controlled as desired by changing the area of contact with air, more specifically, by changing the oxygen diffusion/permeability.

The thermal pack of the present invention consist of at least one continuous layer of a material which exhibits the thermophysical characteristics specified herein. Continuous layer or layers of one or more such materials are typically included as one or both of the layers used to form the heat cells. Alternatively, the heat cells may be cut apart individually or in groups and mounted against one or more continuous layers of a material which exhibits the thermophysical characteristics specified herein.

The thermal pack of the present invention may optionally incorporate a component, such as a separate substrate layer or incorporated into at least one of the continuous layers, comprising active aromatic compounds, non-active aromatic compounds, pharmaceutical actives or other therapeutic agents, and mixtures thereof, to be delivered through the skin. Such active aromatic compounds include, but are not limited to, menthol, camphor, and eucalyptus. Such non-active aromatic compounds include, but are not limited to, benzaldehyde, citral, decanal, and aldehyde. Such pharmaceutical actives/therapeutic agents include, but are not limited to antibiotics, vitamins, antiviral agents, analgesics, anti-inflammatory agents, antipruritics, antipyretics, anesthetic agents, antifungals, antimicrobials, and mixtures thereof The thermal pack may also comprise a separate substrate layer, or incorporated into at least one of the continuous layers, a self-adhesive component and/or a sweat-absorbing component.

The thermal pack of the present invention can be used alone or can be incorporated into various wraps or pads. Typically, these wraps have a means for retaining wraps or pads in place around various parts of the body, such as knee, neck, back, abdomen, etc. and can comprise any number of styles and shapes.

The finished thermal pack is typically packaged in a secondary package. An air-impermeable package may be used to prevent an oxidation reaction from occurring until desired as described in the aforementioned U.S. Pat. No. 4,649,895, already incorporated herein by reference. Alternatively, other means may also be used to prevent an oxidation reaction from occurring before desired, such as air impermeable removable adhesive strips can be placed over the aeration holes in the heat cells such that, when the strips are removed, air is allowed to enter the heat cell, thus activating the oxidation reaction of the iron powder.

What is claimed is:

1. A disposable thermal pack having a unified structure comprising:

a.) at least one continuous layer of a coextruded material having a first side of polypropylene and a second side of a low melt temperature copolymer, wherein said continuous layer is semirigid having at least two dimensional drape at a temperature of about 25° C. and substantially less rigid having at least three dimensional drape at a temperature of about 45° C.; and b.) a plurality of individual heat cells spaced apart and fixedly attached to at least one of said at least one continuous layer to form said unified structure of said thermal pack.

2. A disposable thermal pack according to claim 1 wherein said continuous layer comprises a coextruded film having a first side of polypropylene and a second side of ethylene vinyl acetate copolymer, wherein said polypropylene comprises from about 10% to about 90% of the total thickness of said film.

3. A disposable thermal pack according to claim 2 wherein said continuous layer comprises a coextruded film having a first side of polypropylene and a second side of ethylene vinyl acetate copolymer, wherein said polypropylene comprises from about 40% to about 60% of the total thickness of said film.

4. A disposable thermal pack according to claim 3 wherein said continuous layer has a thickness of from about 20 $\mu$m to about 30 $\mu$m.

5. A disposable thermal pack according to claim 4 wherein said heat cells are placed into positions, along said continuous layer, relative to each other which are sufficiently close so that the number of axes which may form across said at least one continuous layer, and which otherwise would have passed uninterrupted between said heat cells, through said thermal pack, or select regions thereof, are reduced or eliminated, causing said thermal pack to fold along a mutliplicity of short interconnected fold lines oriented in a number of different directions relative to each other, thus minimizing or eliminating undesirable, two dimensional drape characteristics across said thermal pack and converting said thermal pack to possess an apparent three dimensional drape characteristic.

6. A disposable thermal pack according to claim 4 wherein said heat cells comprise an exothermic composition which comprises:

a.) from about 30% to about 80% by weight, iron powder;
b.) from about 3% to about 25% by weight, activated carbon, non-activated carbon, and mixtures thereof;
c.) from about 0.5% to about 10% by weight, metal salt; and
d.) from about 1% to about 40% by weight, water.

7. A disposable thermal pack according to claim 6 wherein said heat cells comprise from about 0.1% to about 30% by weight, of additional water-holding material.

8. A disposable thermal pack according to claim 6 wherein said heat cells comprise a shape selected from the group consisting of a disk, triangle, pyramid, cone, sphere, square, cube, rectangle, rectangular parallelepiped, cylinder, and ellipsoid.

9. A disposable thermal pack according to claim 8 wherein said heat cells comprise the shape selected from the group consisting of a disk and ellipsoid, wherein said disk has a diameter of from about 2 cm to about 3 cm and a height of from about 0.4 cm to about 0.8 cm and said ellipsoid has a width at its widest point of from about 0.15 cm to about 10 cm, a length at its longest point of from about 1 cm to about 10 cm, and a height at its highest point of from about 0.15 cm to about 1 cm, and wherein said heat cells have a fill volume to cell volume ratio of from about 0.7 to about 1.0.

10. A disposable thermal pack according to claim 1 wherein said heat cells comprise an exothermic composition which comprises:

a.) from about 30% to about 80% by weight, iron powder;
b.) from about 3% to about 20% by weight, of carbonaceous material selected from the group consisting of activated carbon, non-activated carbon, and mixtures thereof;
c.) from about 0.5% to about 9% by weight, of an agglomeration aid selected from the group consisting of corn syrup, maltitol syrup, crystallizing sorbitol syrup, amorphous sorbitol syrup, and mixtures thereof; and
d.) from about 4% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;

wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof.

11. A disposable thermal pack according to claim 10 wherein said heat cells further comprise from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

12. A disposable thermal pack according to claim 10 wherein said dry binder comprises from about 4% to about 30% by weight, of microcrystalline cellulose.

13. A disposable thermal pack according to claim 10 wherein said metal salt comprises sodium chloride.

14. A disposable thermal pack according to claim 10 wherein said heat cells are activated by the addition of an aqueous solution.

15. A disposable thermal pack according to claim 10 wherein said direct compaction articles are selected from the group consisting of granules, pellets, tablets, slugs, and mixtures thereof wherein said tablets and slugs comprise a geometric shape selected from the group consisting of disk, triangle, square, cube, rectangle, cylinder, and ellipsoid.

16. A disposable thermal pack according to claim 15 wherein said tablets and slugs comprise a disk shaped geometry having a diameter of from about 0.2 cm to about 10 cm and a height of from about 0.08 cm to about 1.0 cm.

17. A disposable thermal pack according to claim 16 wherein said tablets comprise a geometric shape selected from the group consisting of a disk shape wherein a hole passes perpendicular to and through the middle of the top and bottom surfaces and a disk shape wherein the top and bottom surfaces are concaved forming a reservoir conducive to holding a liquid.

18. A disposable thermal pack according to claim 17 wherein said tablets comprise a disk shape wherein a hole passes perpendicular to and through the middle of the top and bottom surfaces.

19. A disposable thermal pack according to claim 15 wherein said direct compaction articles comprise a density of greater than about 1 g/cm$^3$.

20. A disposable thermal pack according to claim 19 wherein said direct compaction articles comprise a density of from about 1.5 g/cm$^3$ to about 3.0 g/cm$^3$.

21. A disposable thermal pack according to claim 9 wherein said heat cells comprise the shape of a disk.

22. A disposable thermal pack according to claim 9 wherein said heat cells comprise the shape of an ellipsoid.

23. A disposable thermal pack according to claim 15 wherein said heat cells comprise a shape selected from the group consisting of a disk, triangle, pyramid, cone, sphere, square, cube, rectangle, rectangular parallelepiped, cylinder, and ellipsoid.

* * * * *